United States Patent [19]
Dutcher et al.

[11] Patent Number: 5,179,962
[45] Date of Patent: Jan. 19, 1993

[54] CARDIAC LEAD WITH RETRACTIBLE FIXATORS

[75] Inventors: Robert G. Dutcher, Minneapolis; Brian M. Packard, Monticello; Robert J. Scott, Minneapolis, all of Minn.

[73] Assignee: Possis Medical, Inc., Minneapolis, Minn.

[21] Appl. No.: 718,377

[22] Filed: Jun. 20, 1991

[51] Int. Cl.$^5$ .............................................. A61N 1/05
[52] U.S. Cl. ................................... 128/785; 128/786; 128/642
[58] Field of Search .................. 128/784-786, 128/419 P, 642

[56] References Cited
U.S. PATENT DOCUMENTS

| | | |
|---|---|---|
| 3,416,534 | 12/1968 | Quinn . |
| 3,754,555 | 8/1973 | Schmitt . |
| 3,902,501 | 9/1975 | Citron et al. . |
| 3,943,936 | 3/1976 | Rasor et al. . |
| 3,976,082 | 8/1976 | Schmitt ............................ 128/785 |
| 4,233,992 | 11/1980 | Bisping . |
| 4,258,724 | 3/1981 | Balat et al. . |
| 4,280,512 | 7/1981 | Karr et al. . |
| 4,378,023 | 3/1983 | Trabucco . |
| 4,408,604 | 10/1983 | Hirshorn et al. .................... 128/785 |
| 4,463,754 | 8/1984 | Gold . |
| 4,502,492 | 3/1985 | Bornzin .............................. 128/785 |
| 4,570,642 | 2/1986 | Kane et al. . |
| 4,628,943 | 12/1986 | Miller . |
| 4,649,938 | 3/1987 | McArthur . |
| 4,662,382 | 5/1987 | Sluetz et al. . |
| 4,762,136 | 8/1988 | Baker, Jr. . |
| 4,943,289 | 7/1990 | Goode et al. . |
| 5,003,992 | 4/1991 | Holleman et al. ................. 128/785 |

Primary Examiner—Lee S. Cohen
Attorney, Agent, or Firm—Burd, Bartz & Gutenkauf

[57] ABSTRACT

A cardiac lead has an electrode and fixation assembly including a plurality of fixation members movable to extended positions into heart tissue to retain the electrode in intimate engagement with heart tissue. An elongated stylet is used to move the fixation members to their extended positions into the heart tissue and retract the fixation members into the fixation assembly to allow the lead to be removed from the heart and body of a person.

37 Claims, 5 Drawing Sheets

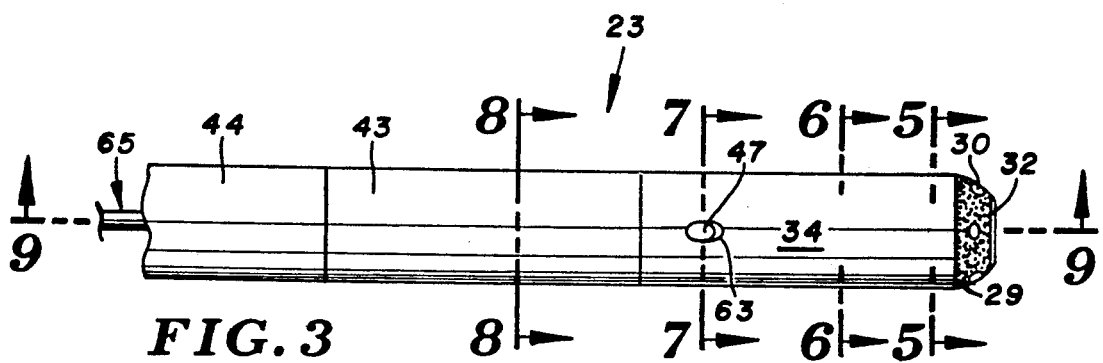
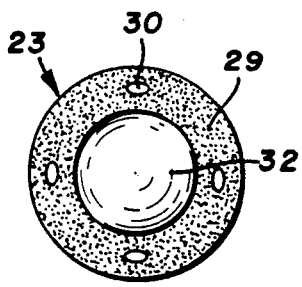
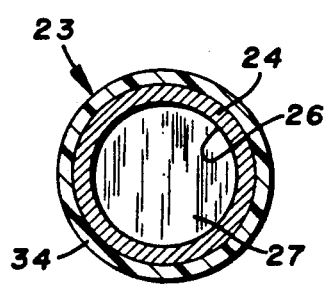
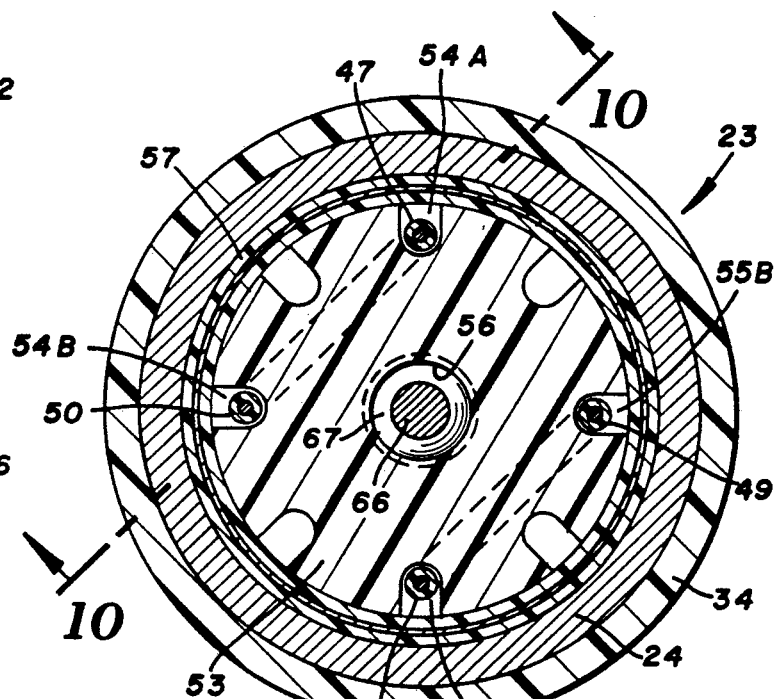
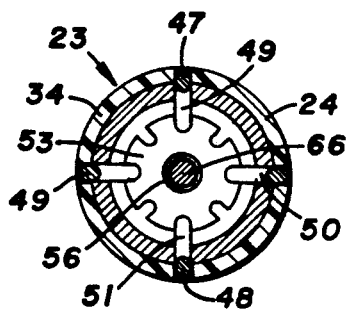
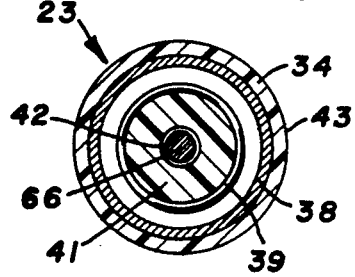

CARDIAC LEAD WITH RETRACTIBLE FIXATORS

FIELD OF THE INVENTION

The invention relates to cardiac leads having fixation members connectable to heart tissue for transmitting electric current to the heart and monitoring the electrical activity of the heart.

BACKGROUND OF THE INVENTION

Cardiac pacing leads having tines that engage heart tissue and urge electrodes into contact with the endocardium in a direction parallel to the lead axis are disclosed by G. A. Bornzin in U.S. Pat. No. 4,502,492 and J. E. Sluetz et al in U.S. Pat. No. 4,662,382. Fibrotic growth of heart tissue around the electrode and tines prevent removal of the electrode from the heart without substantial damage to the heart. A corkscrew connected to an electrode is disclosed by R. G. Baker in U.S. Pat. Nos. 4,679,572 and 4,762,136 to provide active fixation of the electrode to the myocardium. The electrode must be rotated to attach and remove the electrode from the heart tissue. Structures used to rotate the electrodes having corkscrew attachment devices as shown by S. L. Miller in U.S. Pat. No. 4,628,943 and W. A. McArthur in U.S. Pat. No. 4,649,938. Fibrotic growth of heart tissue around electrode and corkscrew. Forced rotation of the electrode and corkscrew can cause heart tissue damage. Another structure for implanting an electrode to heart tissue is disclosed by G. Schmitt in U.S. Pat. No. 3,754,555 and D. E. Karr et al. This structure has a pair of resilient prongs or wire springs projected from the distal end of the electrode into the heart tissue. The springs are enclosed within a sleeve to permit insertion of the electrode into the heart. When the electrode is positioned in contact with the endocardium, a stylet is used to move the springs forwardly out of the sleeve into the heart tissue. The stylet is also used to pull the springs back into the sleeve to retract the springs from the heart tissue.

SUMMARY OF THE INVENTION

The invention relates to a cardiac lead connectable to an implantable cardiac arrhythmia management device for transmitting electric current to the heart and/or sensing and monitoring the electrical activity of the heart. The implantable cardiac arrhythmia management device includes but is not limited to cardiac pacemakers and automatic implantable cardiac defibrillators (AICD). The lead has an elongated flexible conductor enclosed within a sheath of nonelectrically conductive material to electrically connect the cardiac management device with an electrode having a distal surface adapted to be implanted in endocardium of the heart. A tissue fixation assembly is operatively associated with the electrode to retain the electrode in contact with the endocardium of the heart. The fixation assembly has a plurality of fixation members adapted to linearly move from a position within the electrode into the endocardium to retain the electrode surface in engagement with the stimulatable heart tissue. The fixation members are mounted on a movable body located within a chamber in the electrode. A stylet cooperates with the body to move the body and fixation members to a position wherein the fixation members project laterally and rearwardly from the electrode. The extended fixation members retain the electrode in engagement with the endocardium. The stylet is also used to retract the fixation members from the endocardium back into the electrode to permit removal of the electrode from the heart with a minimum of damage to the heart tissue. The electrode is an annular member of electrically conductive metal, such as titanium, platinum, platinum iridium or carbon, having an annular non-flat surface that can be coated with platinum black particles which contact the heart tissue. Other type of coatings including but not limited to Pyrolitic carbon, titanium nitride, and the like can be used to enhance the electro-tissue interface between the electrode and heart tissue and to maximize voltage applied to the heart and minimize electrical resistance between the electrode and the heart tissue.

These and other objects and advantages of the cardiac lead of the invention are embodied in the following detailed description and drawings.

DESCRIPTION OF THE DRAWING

FIG. 3 is an enlarged top view of the electrode end of the lead showing the retracted fixation members;

FIG. 4 is an enlarged distal end view of the electrode end of FIG. 3;

FIG. 5 is an enlarged sectional view taken along line 5—5 of FIG. 3;

FIG. 6 is an enlarged sectional view taken along line 6—6 of FIG. 3;

FIG. 7 is an enlarged sectional view taken along line 7—7 of FIG. 3;

FIG. 8 is an enlarged sectional view taken along line 8—8 of FIG. 3;

FIG. 1 is an enlarged sectional view taken along line 10—10 of FIG. 6;

DESCRIPTION OF PREFERRED EMBODIMENT

Figure 1:
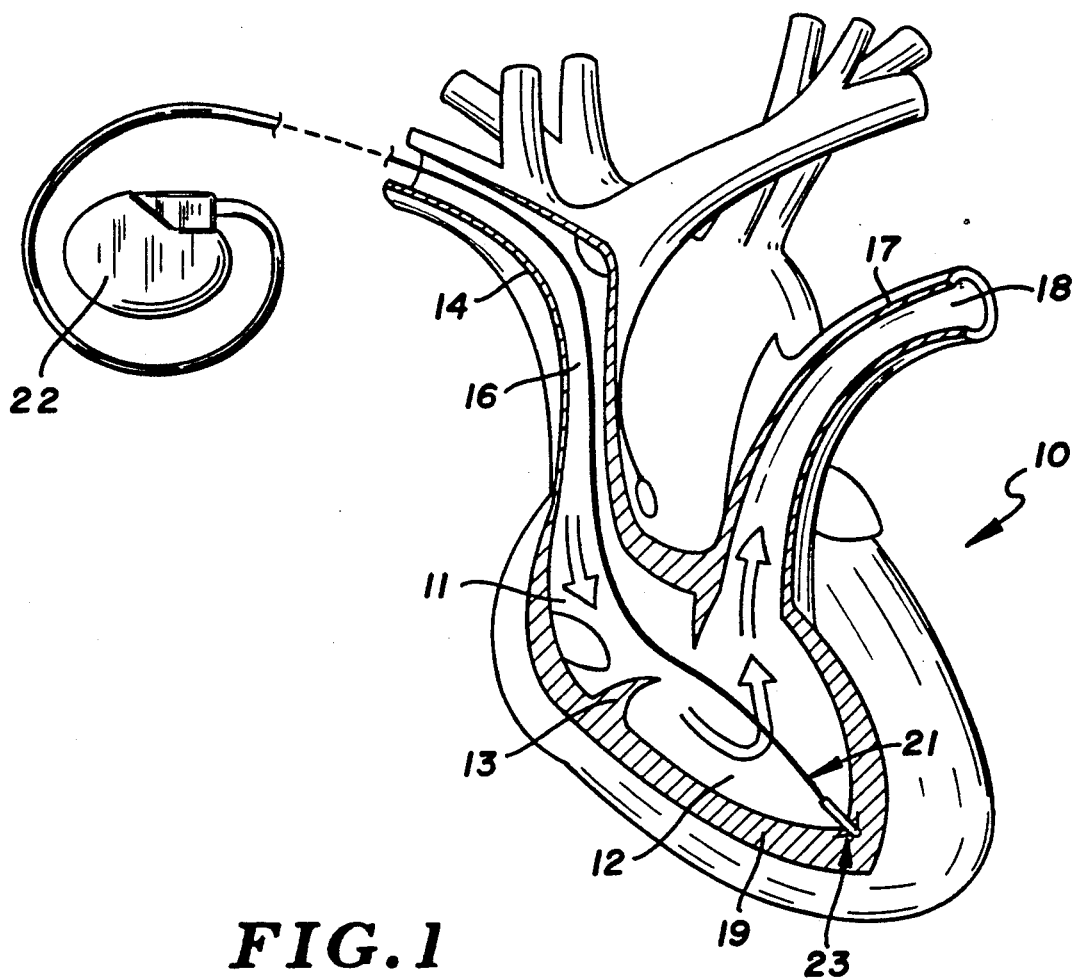
FIG. 1 is a diagrammatic view of a cardiac management system having the cardiac lead of the invention implanted in the right ventricle of a human heart.
Figure 2:
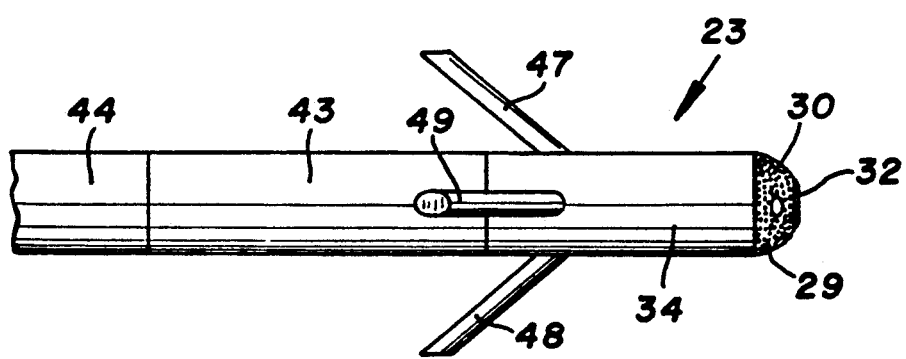
FIG. 2 is a side view of the electrode end of the lead showing the extended fixation members thereof.

Referring to FIG. 1, there is shown a human heart indicated generally at 10 provided with a cardiac arrhythmia management device 22, such as a pacemaker, pulse generator, and an implantable cardiac defibrillator having a removable lead indicated generally at 21 of the invention. Heart 10 is shown as having a right atrium 11, a right ventricle 12 and a heart valve 13 for controlling the flow of blood from right atrium 11 into right ventricle 12. A supply of blood flows in vein 14 having lumen 16 to right atrium 11. The blood flows from right ventricle 12 through a pulmonary artery 17 having a lumen 18 open to right ventricle 12.

Lead 21 is connected to a cardiac arrhythmia management device 22 located within the human body outside of heart 10 for transmitting electric current to the heart and/or sensing and monitoring the electrical activity of the heart. Lead 21 has a fixation assembly indicated generally at 23 located partly within the trabecular carneae and/or apex of endocardium 19 in right ventricle 12.

Figure 9:
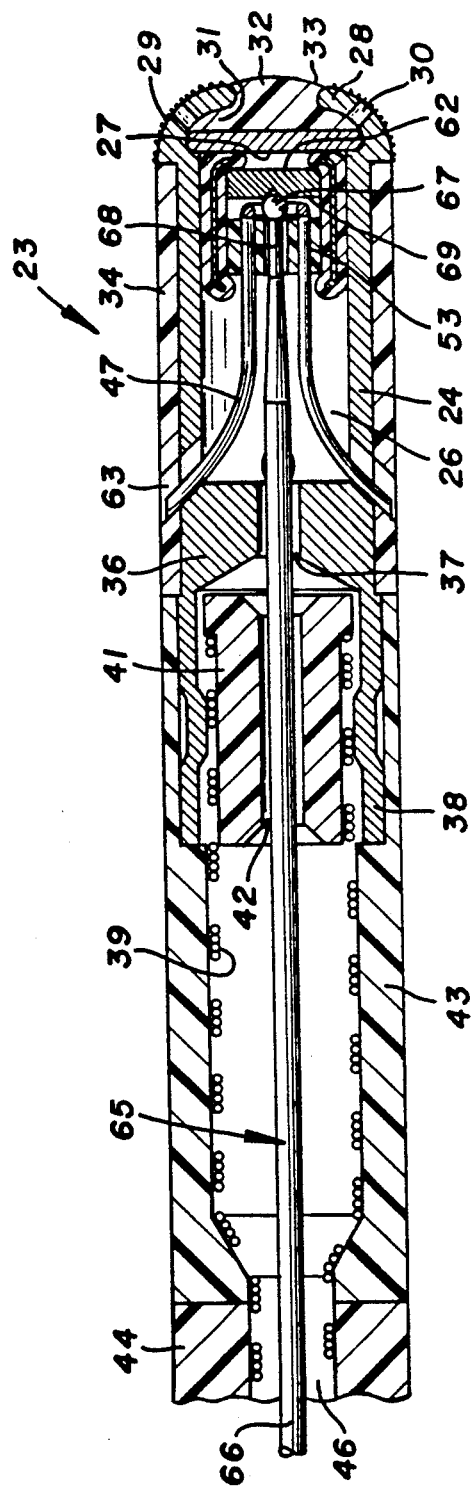
FIG. 9 is an enlarged sectional view taken along line 9—9 of FIG. 3.

Referring to FIG. 9, fixation assembly 23 has an elongated cylindrical body 24 of electrically conductive material, such as metal and like conductors. Body 24 has a longitudinal chamber 26 closed at its distal or forward end with a disc 27. Body 24 has an annular form or lip 28 turned inwardly over disc 27 to retain disc 27 in body 24. Lip 28 is also turned over insert 32 to retain insert 32 on the forward end of body 24. As shown in FIGS. 3 and 4, form 28 has an annular arcuate outer surface that is coated with platinum black particles 29. Form 28 has a plurality of circumferentially spaced holes 30 open to the outer surface thereof for additional ingrowth of tissue to assist in anchoring form 28 to endocardium 19. The platinum black particles 29 have microporous structure which allows the distal end of the electrode to be located in close proximity to the stimulatable heart tissue. This increases the current density to the tissue and lowers stimulation thresholds. The microsurface porous black particles 29 results in growth of a thinner fibrotic capsule surrounding the electrode and fixation assembly. Other types of electrical conductive materials, such as Pyrolitic carbon and titanium nitride, can be secured to the annular outer surface of form 28.

Form 28 surrounds a recess 31 that is closed with insert 32. Insert 32 has a convex exterior surface 33 that is coextensive with the outer surface of form 28 coated with platinum black particles 29. The outer surface 33 of insert 32 can have other configurations, such as flat, concave or the like. Insert 32 is a bio-compatible plastic, such as silicone rubber, synthetic fabric including but not limited to woven polyester, Teflon and the like.

A jacket or sleeve 34 of electrical insulating material, such as bio-compatible plastic, ceramic or silicone rubber, surrounds body 24 so that only the platinum black particles 29 make electrical contact with the endocardium.

Body 24 has a transverse neck 36 having a central hole 37 open to chamber 26. A tubular end 38 joined to neck 36 is connected to an electrical conductor 39 shown as a wire coil. A retainer 41 positioned within tubular end 38 holds the distal end of conductor 39 in electrical contact with tubular end 38. Retainer 41 has a central hole or passage 42 in alignment with hole 37 and neck 36. Conductor 39 is located within a connector 43 joined to an elongated flexible tubular sheath 44. Connector 43 is a tubular electrical insulator, such as plastic, silicone rubber and the like. Sheath 44 is an elongated tube of biocompatible and non-electrical conductive material that extends from electrode and fixation assembly 23 to cardiac arrhythmia management device 22. Coil 39 is located within the longitudinal passage 46 of sheath 44 which leads to cardiac arrhythmia management device 22.

Figure 10:
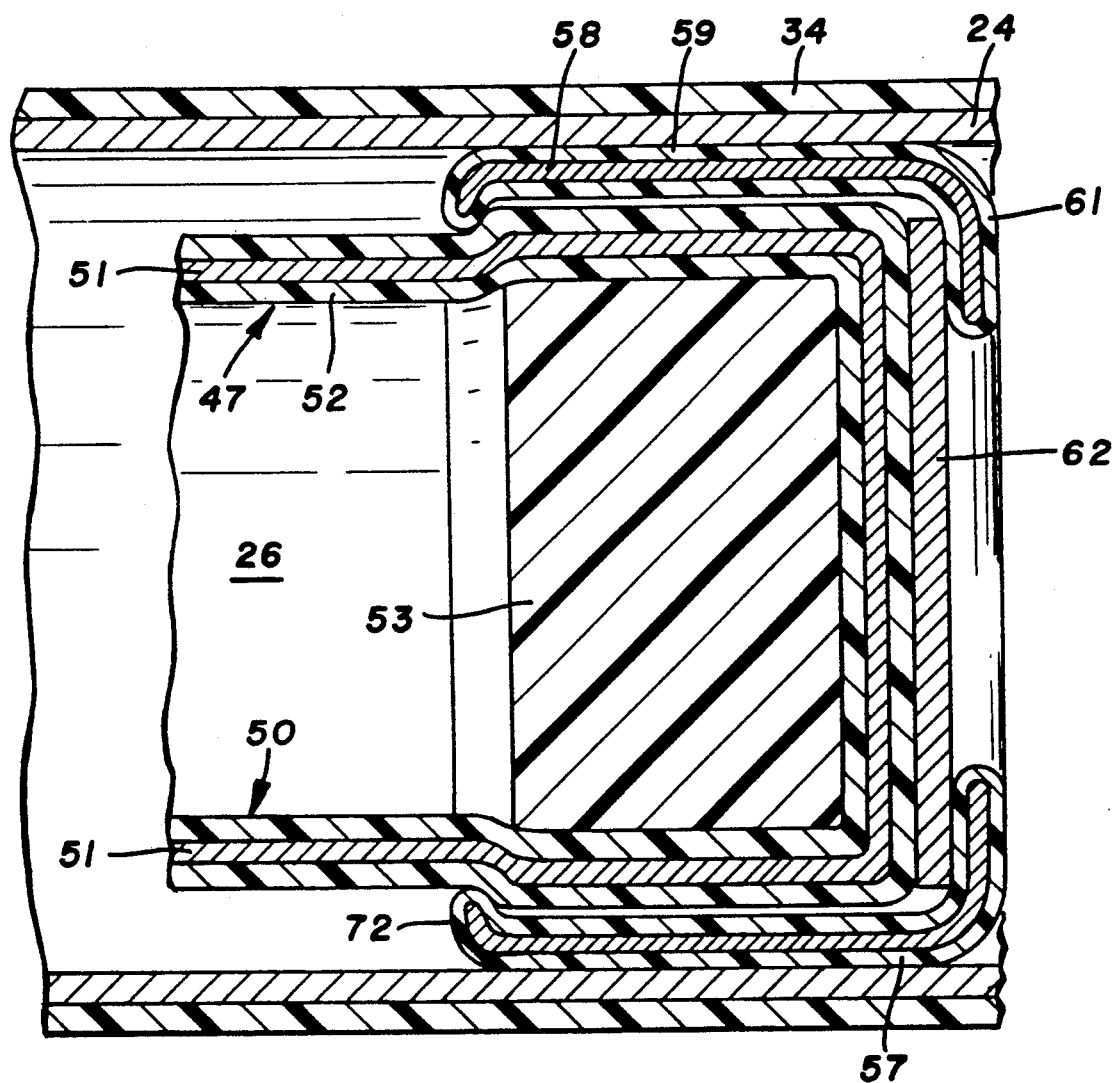

Fixation assembly 23 has a plurality of fixation members having elongated wire-like structures that are movable into the heart tissue to retain form 28 of the electrode in intimate contact with the heart tissue and retractable into body 24 to allow the lead to be removed from the heart. Fixation assembly 23 has four fixation members 47-50. Fixation members 47-50 are metal rods coated with non-electrical conductive material, such as bio-compatible plastic. As shown in FIG. 10, fixation members 47 and 50 are ends of the U-shaped flexible wire or rod 51 embedded within a layer or coat 52 of bio-compatible plastic material. The entire wire 51 is covered with coat 52 so that fixation members 47 and 50 are non-electrically conductive. Fixation members 48 and 49 have the same shape and structure as fixation members 47 and 50.

As shown in FIG. 6, fixation members 47-50 are positioned on a tubular member or ring 53 of medical grade plastic, such as polycarbonate. Ring 53 has a first pair of grooves 54A and 54B accommodating fixation members 47 and 50 and a second pair of grooves 55A and 55B accommodating fixation members 48 and 49. Grooves 54A, 54B, 55A, and 55B circumferentially space fixation members 47-50 around ring 53. As seen in FIG. 7, ring 53 has additional open grooves to relieve any hydraulic effects due to fluid in chamber 26. The center of ring 53 has a circular hole 56.

An annular sleeve 57 surrounds ring 53 to hold fixation members 47-50 in grooves 54A, 54B, 55A, and 55B. Returning to FIG. 10, sleeve 57 has a metal core 58 coated with bio-compatible plastic material 59. The distal end 61 of sleeve 57 is turned inwardly over a disk 62 located in front of ring 53. The opposite end 72 of sleeve 57 is turned inwardly over ring 53 to clamp fixation members 47-50 onto ring 53.

Electrode and fixation assembly 23 can be provided with additional fixation members which are extendable into the endocardium and retractable therefrom. For example, two additional pairs of fixation members circumferentially spaced between fixation members 47-50 can be used with the electrode and fixation assembly 23. Alternatively, fixation assembly can have one pair of fixation members. The number of fixation members can vary.

As shown in FIG. 9, fixation members 47-50 when in retraced positions have outer ends located in openings 63 in body 24 adjacent neck 36. Sleeve 34 may have openings to allow fixation members 47-50 to be moved to their extended positions as shown in FIGS. 1, 2, 11, 12, and 13. The openings in sleeve 34 can be formed by the fixation members 47-50 as they are moved to the extended position. Openings 63 are inclined rearwardly to guide fixation members 47-50 outwardly and rearwardly from body 24. Neck 36 has beveled outer edges 64 that serve as ramps or guiding surfaces for fixation members 47-50 during movement thereof to the extended positions. As shown in FIGS. 2, 11, 12, and 13, fixation members 47-50 project rearwardly at an angle of about 45 degrees from the longitudinal axis of the electrode and fixation assembly 23. Other angular orientations of fixation members 47-50 can be used.

Figure 12:
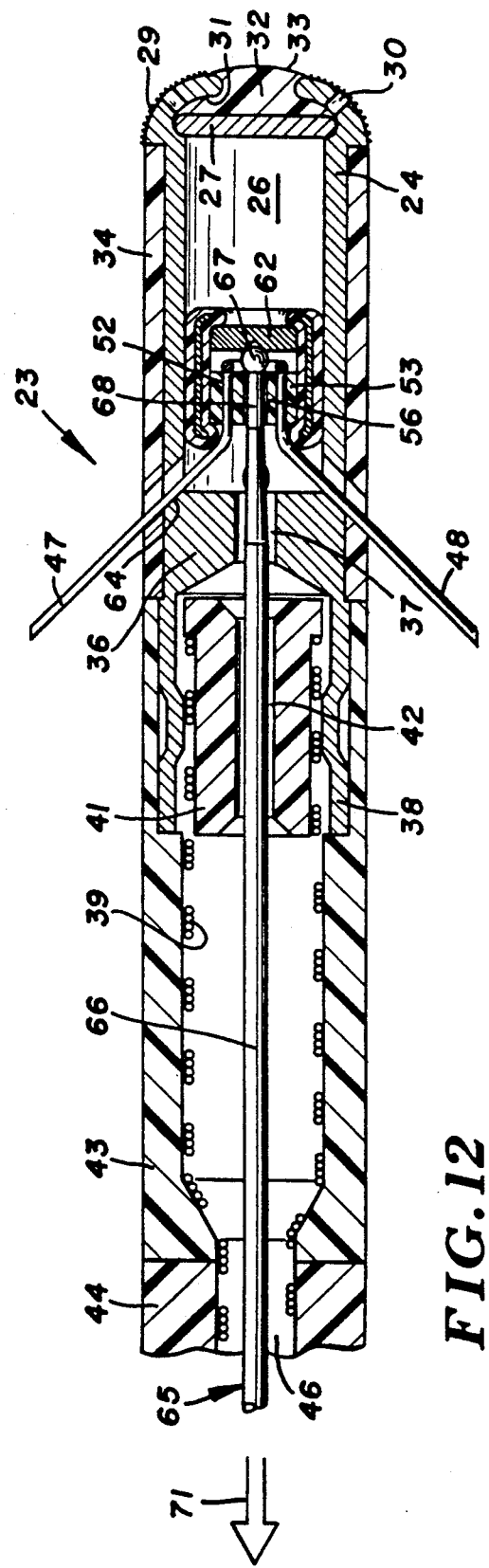
FIG. 12 is an enlarged sectional view taken along the line 12—12 of FIG. 11.

An elongated stylet indicated generally at 65 is used to move fixation members 47-50 between their retracted positions, as shown in FIG. 9, and their extended positions, as shown in FIG. 12. As shown in FIGS. 9 and 12, stylet 65 has an elongated body or wire 66 terminating in a spherical head 67 at the distal end thereof. A short tapered neck 68 having a diameter less than the diameter of hole 56 and ring 53 joins head 67 to wire 66. Head 67 has a diameter larger than the diameter of hole 56. Head 67 has a snap fit relative to ring 53 whereby head 67 can be forced through hole 56 and pulled out of hole 56 so that stylet 64 can be removed from pacing lead 21.

Figure 11:
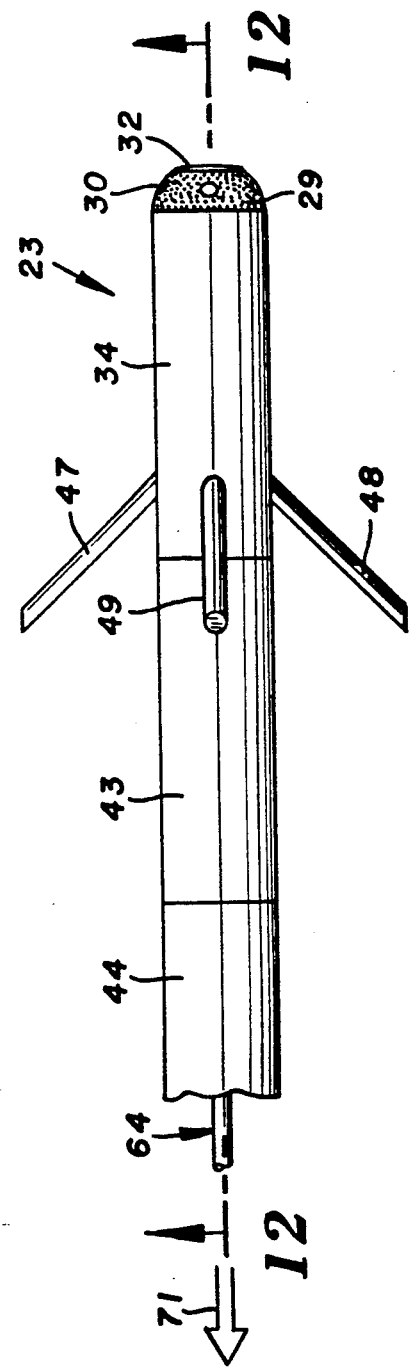
FIG. 11 is a top view of the electrode end of the lead showing the extended fixation members.
Figure 13:
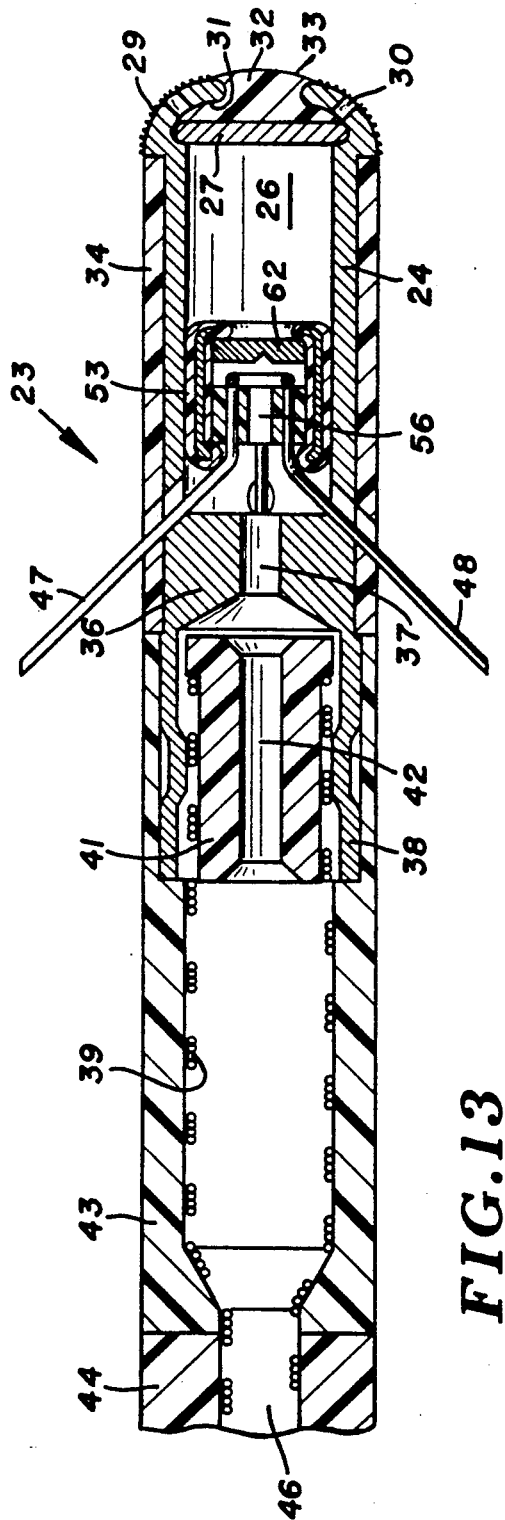
FIG. 13 is a sectional view similar to FIG. 12 with the stylet removed from the lead.

As shown in FIG. 9, stylet 65 is located in passage 46 of sheath 44 and extends through hole 42 in retainer 41, hole 37 in neck 36, through chamber 26 with head 67 located in a space between ring 53 and disk 62. Fixation members 47-50 are in their retracted positions within body 24 whereby the electrode and fixator assembly 23 has a generally outside cylindrical configuration which permits the lead to be implanted in and removed from the heart with a minimum of damage to the heart tissue. Lead 21 is implanted into the heart of right ventricle 12 in engagement with endocardium 19 at the base of ventricle 12 as shown in FIG. 1, by threading the lead through lumen 16 of vein 14, atrium 11, and ventricle 12. The active surface of the electrode coated with the platinum black particles 29 is located in intimate contact with the endocardium. Stylet 65 is then pulled as indicated by the arrow 71 in FIG. 11 and 12 by the physician while sheath 44 and the remainder of the electrode and fixation assembly 23 is held in position. Ring 53 along with fixation members 47-50 are moved to their extended positions as shown in FIG. 11 with fixation members 47-50 projecting into the heart tissue. The rearward inclination of fixation members 47-50 retain electrode surface 29 in firm and intimate contact with the endocardium. Stylet 65 moves ring 53 rearwardly to a position adjacent neck 36. Continued pulling force on stylet 65 snaps head 67 from ring 53 so that the entire stylet 65 is removed from lead 21. FIG. 13 shows the electrode and fixation assembly 23 with fixation members 47-50 in their extended positions with stylet 65 removed from pacing lead 21.

Stylet 65 is also used to retract fixation members 47-50 from the endocardium. Wire 66 and head 67 is threaded through passage 46 of sheath 44, hole 42 in retainer 41, and hole 37 in neck 36. Head 67 is forced through the hole 56 in ring 53 into engagement with disk 62. Further inward movement of stylet 65 into pacing lead forces ring 53 and fixation members 47-50 to move forwardly whereby fixation members 47-50 move into chamber 26 of body 24 as shown in FIG. 9. Fixation members 47-50 retract linearly in the direction of their length from the heart tissue thereby minimizing injury to the heart tissue. When fixation members 47-50 are in their retracted positions, the outer surface of electrode and fixation assembly 23 is cylindrical and smooth. This permits the entire lead 21 to be removed from the heart and body of the person.

While there has been shown and described a cardiac lead having retractable fixation members, it is understood that changes, additions, and arrangements of structures may be made by those skilled in the art without departing from the invention.

We claim:

1. An implantable lead comprising: an electrical conductor having a first end adapted to be connected to a cardiac arrhythmia management device and a second end, a sheath of insulative material covering said conductor, and an electrode and fixation assembly connected to the second end of the conductor and the sheath, said electrode and fixation assembly including a body having a chamber, said body being an electrical conductor member connected to the electrical conductor, said body having a distal end including and outer surface for directly containing the endocardium of the heart, a jacket of electrical insulation material covering the body except for said outer surface, carrier means located within the chamber for movement between first and second positions; at least one fixation means moveable from a first position within the assembly to a second position extended away from the assembly for engagement with the endocardium of the human heart, means mounting said fixation means on the carrier means whereby the fixation means moves with the carrier means, said body and jacket having hole means open to the chamber accommodating the fixation means to allow the fixation means to be moved from the chamber outwardly of the body into the endocardium of the heart and moved inwardly into the body out of engagement with the endocardium of the heart, said carrier means cooperating with means operable to selectively move the carrier means to the first and second positions to extend and retract the fixation means relative to the body.

2. The lead of claim 1 including: platinum black particles covering the outer surface of the body.

3. The lead of claim 1 wherein: the outer surface of the body is a surface having a plurality of holes.

4. The lead of claim 3 including: platinum black particles covering the surface.

5. The lead of claim 1 wherein: the fixation means comprise a plurality of elongated members.

6. The lead of claim 1 wherein: the fixation means comprise two pairs of elongated members circumferentially spaced around the electrode and fixation assembly.

7. The lead of claim 1 wherein: the fixation means comprises a plurality of flexible wire members covered with non-electrical conductive material.

8. The lead of claim 1 wherein: said carrier means has ring means having grooves accommodating portions of the fixation means, said means mounting the fixation means on the carrier means comprises a sleeve located around the ring means to retain the portions of the fixation means in said grooves.

9. The lead of claim 8 wherein: the fixation means are U-shaped flexible wire members covered with non-electrical conductive material having first portions located in said grooves and second end portions moveable from the chamber outwardly of the body into the endocardium of the heart and inwardly into the body out of engagement with the endocardium of the heart.

10. The lead of claim 1 wherein: the fixation means comprises a plurality of elongated fixation members mounted on the carrier means, said hole means comprising a plurality of holes open to the chamber, each of the holes accommodating a fixation member whereby the fixation members move through said holes to their extended positions into the endocardium of the heart.

11. The lead of claim 10 wherein: four fixation means are mounted on the carrier means, said body and jacket having four of said holes for accommodating said four fixation members.

12. The lead of claim 1 wherein: the carrier means has a central hole, said means operable to move the fixation means comprises an elongated stylet having a head larger than the hole whereby when the head is forced through the hole, the stylet can be moved relative to the body to move said carrier means between said first and second position thereby moving the fixation means to said extended and retracted positions.

13. The lead of claim 1 wherein: said carrier means includes ring means for supporting the fixation means, and the means mounted said fixation means on the carrier means comprises a sleeve located around the ring means to retain the fixation means on the ring means.

14. The lead of claim 1 wherein: said means for selectively moving the fixation means comprising a stylet extended through said sheath and into the chamber of the body, said stylet and carrier means having cooperating means releasably connecting the stylet to the carrier means whereby the stylet is moved to move the carrier means between its first and second positions to extend and retract the fixation means relative to the body.

15. The lead of claim 1 wherein: the body has a cylindrical side wall surrounding said chamber and a distal end having said outer surface, said jacket surrounding said side wall, said side wall and jacket having said hole means accommodating the fixation means whereby the fixation means project laterally from the body when the fixation means are in the second position.

16. The lead of claim 15 wherein: the hole means are inclined rearwardly to guide the fixation means outwardly and rearwardly from the body to the second position thereof.

17. The lead of claim 15 wherein: the fixation means has a plurality of flexible elongated wire members covered with non-electrical conductive material.

18. An implantable lead comprising: an electrical conductor having a first end adapted to be connected to a cardiac arrhythmia management device and a second end, a sheath of insulative material covering said conductor, and an electrode and fixation assembly connected to the second end of the conductor and the sheath, said electrode and fixation assembly including an electrical conductive body means connected to the electrical conductor having an outer surface for directly contacting the endocardium of the heart, fixation means mounted on the body means for movement from a retracted position within the body means to an extended position away from the body means to retain the outer surface of the body means in contact with the endocardium of the heart, said body means having an internal chamber, and hole means in said body means open to the chamber to accommodate the fixation means, a member located within said chamber moveable between first and second positions, said fixation means being located within said chamber and having elongated portions located in said hole means, means mounting the fixation means on the member for movement with the member into said retracted position in the chamber and said extended position away form said body means into engagement with the endocardium of the heart, said means mounting the fixation means on the member comprises a sleeve located around the member, said member cooperating with the means operable to move the member between said first and second positions thereby selectively moving the fixation means to its extended position and retracted position.

19. The lead of claim 18 including: platinum black particles covering the outer surface of the body means.

20. The lead of claim 18 wherein: the fixation means comprise a plurality of elongated members covered with non-electrical conductive material.

21. The lead of claim 18 wherein: the fixation means comprise a plurality of elongated members circumferentially spaced around the body means, each elongated member having a portion located in said hole means in the body means and moveable between a retracted position within the body means to an extended position into the endocardium of the heart.

22. The lead of claim 19 wherein: the member has a central hole, said means operable to move the member comprises an elongated stylet having a head larger than the hole whereby when the head is forced through the hole the stylet can be moved relative to the body means to move the member between said first and second positions thereby moving the fixation means to its extended position and retracted position.

23. The lead of claim 23 wherein: the outer surface of the body means is an annular surface.

24. The lead of claim 23 wherein: platinum black particles covering the annular surface.

25. The lead of claim 18 wherein: the outer surface of the body means has a plurality of holes.

26. The lead of claim 25 including: platinum black particles covering said outer surface of the body means.

27. The lead of claim 18 wherein: the member has groove means accommodating portions of the fixation means, and a sleeve located around the member retaining the portions of the fixation means in said groove means.

28. The lead of claim 27 wherein: the fixation means are U-shaped flexible wire members covered with non-electrical conductive material having first portions located in said groove means and second end portions moveable from the chamber outwardly through said hole means into engagement with the endocardium of the heart.

29. The lead of claim 18 wherein: the body means have a cylindrical side wall surrounding the chamber, and non-electrical conductor means surrounding said side wall and mounted thereon, said side wall and non-electrical conductor means having said hole means whereby the elongated portions of the fixation means project laterally from the body means when the fixation means are in the extended position.

30. The lead of claim 29 wherein: the hole means are inclined rearwardly to guide the elongated portion of the fixation means outwardly and rearwardly from the body means to the extended position thereof.

31. An implantable lead comprising: an electrical conductor having a first end adapted to be connected to a cardiac arrhythmia management device and a second end, a sheath of insulative material covering said conductor, and an electrode and fixation assembly connected to the second end of the conductor and the sheath, said electrode and fixation assembly including an electrical conductive body means connected to the electrical conductor having an outer surface for directly contacting the endocardium of the heart, fixation means mounted on the body means for movement from a retracted position in the body means and to an extended position away from the body means to retain the outer surface of the body means in contact with the endocardium of the heart, said body means having a cylindrical side wall surrounding an internal chamber, electrical insulation means surrounding the side wall, hole means in the side wall and electrical insulation means open to the chamber to accommodate the fixation means, a member located within said chamber moveable between first and second positions, said fixation means being located within said chamber and having elongated portions located in said hole means, means mounting the fixation means on the member for movement with the member into retracted position in the chamber and an extended position laterally away form said side wall of the body means into engagement with the endocardium of the heart, said member cooperating with means operable to move the member between said first and second position thereby moving the fixation means to its extended position and retracted position.

32. The lead of claim 31 wherein: the fixation means comprise a plurality of elongated members covered with non-electrical conductive material.

33. The lead of claim 31 wherein: the fixation means comprises two pairs of elongated members circumferentially spaced around the body means, each elongated member having a portion located in said hole means in the body means and moveable between a retracted position within the body means to an extended position into the endocardium of the heart.

34. The lead of claim 31 wherein: the means mounting the fixation means on the member comprise a sleeve located around the member.

35. The lead of claim 31 wherein: the member has groove means accommodating portions of the fixation means, said means mounting the fixation means on the member retaining the portions of the fixation means in said groove means.

36. The lead of claim 35 wherein: the fixation means are U-shaped flexible wire members covered with non-electrical conductive material having first portions located in said groove means and second end portions moveable from the chamber outwardly through said hole means into engagement with the endocardium of the heart.

37. The lead of claim 31 wherein: the hole means are inclined rearwardly to guide the elongated portions of the fixation members outwardly and rearwardly from the body means to the extended position thereof.

* * * * *